United States Patent
Myers et al.

(10) Patent No.: US 11,551,817 B2
(45) Date of Patent: Jan. 10, 2023

(54) ASSESSING UNRELIABILITY OF CLINICAL RISK PREDICTION

(71) Applicants: International Business Machines Corporation, Armonk, NY (US); Massachusetts Institute of Technology, Cambridge, MA (US)

(72) Inventors: Paul D. Myers, Cambridge, MA (US); Uri Kartoun, Cambridge, MA (US); Kristen Severson, Somerville, MA (US); Wangzhi Dai, Cambridge, MA (US); Kenney Ng, Arlington, MA (US); Collin M. Stultz, Newton, MA (US)

(73) Assignee: International Business Machines Corporation, Armonk, NY (US)

( * ) Notice: Subject to any disclaimer, the term of this patent is extended or adjusted under 35 U.S.C. 154(b) by 312 days.

(21) Appl. No.: 16/741,991

(22) Filed: Jan. 14, 2020

(65) Prior Publication Data
US 2021/0217529 A1  Jul. 15, 2021

(51) Int. Cl.
| | | |
|---|---|---|
| *G16H 50/30* | (2018.01) | |
| *G16H 50/20* | (2018.01) | |
| *G06K 9/62* | (2022.01) | |
| *G16H 10/60* | (2018.01) | |
| *G16H 10/40* | (2018.01) | |

(52) U.S. Cl.
CPC ........... *G16H 50/30* (2018.01); *G06K 9/6232* (2013.01); *G06K 9/6277* (2013.01); *G16H 10/40* (2018.01); *G16H 10/60* (2018.01); *G16H 50/20* (2018.01)

(58) Field of Classification Search
CPC ........ G16H 50/20; G16H 50/30; G16H 10/40; G16H 10/60; G06K 9/6232; G06K 9/6277; G06V 10/764; G06V 10/7715; G06V 30/19173; G06V 30/19127
USPC ............................................................ 705/3
See application file for complete search history.

(56) References Cited

U.S. PATENT DOCUMENTS

| | | |
|---|---|---|
| 7,853,456 B2 | 12/2010 | Soto et al. |
| 8,031,076 B2 | 10/2011 | Sachanandani et al. |
| 8,090,562 B2 | 1/2012 | Snider et al. |
| 2005/0203773 A1 | 9/2005 | Soto et al. |
| 2009/0264779 A1 | 10/2009 | Snider et al. |
| 2010/0045467 A1 | 2/2010 | Sachanandani et al. |
| 2012/0059779 A1* | 3/2012 | Syed ................. G06N 20/00 706/12 |
| 2016/0364544 A1 | 2/2016 | Das et al. |
| 2017/0147770 A1 | 5/2017 | Xu et al. |
| 2018/0192894 A1 | 7/2018 | Thakur et al. |

(Continued)

FOREIGN PATENT DOCUMENTS

EP         3282258 A1    2/2018

*Primary Examiner* — John P Go
*Assistant Examiner* — Christopher B Wehrly
(74) *Attorney, Agent, or Firm* — Cantor Colburn LLP; Stosch Sabo

(57) ABSTRACT

Aspects of the invention include includes identifying a respective estimated clinical risk score for each of a first group of patients and a second group of patients. An alternative probability estimate is generated using a same set of inputs used to determine each respective estimated clinical risk score. An unreliability of a patient's clinical risk score is determined based at least in part on a feature of the patient and on a difference between the alternative probability estimate and the determined respective estimated clinical risk score.

17 Claims, 5 Drawing Sheets

(56) References Cited

U.S. PATENT DOCUMENTS

2019/0172592 A1  6/2019  Chan et al.
2020/0380882 A1* 12/2020  Alailima ................ G09B 19/00
2021/0151191 A1*  5/2021  Fornwalt ................ G16H 10/60

* cited by examiner

ASSESSING UNRELIABILITY OF CLINICAL RISK PREDICTION

BACKGROUND

The present invention generally relates to health care technology and more specifically, to assessing unreliability of clinical risk prediction.

To provide care for patients, the health care system includes a variety of participants, including doctors, nurses, and other hospital-related personnel. To help clinicians navigate risk assessment, a variety of informatics-based tools have been developed to evaluate potential outcomes associated with treatment options. These risk assessment tools are generally provided by a third-party software, and made available to a clinician through software applications.

SUMMARY

Embodiments of the present invention are directed to assessing the reliability of clinical risk predictions. A non-limiting example computer-implemented method includes identifying a respective estimated clinical risk score for each of a first group of patients and a second group of patients. An alternative probability estimate is generated using a same set of inputs used to determine each respective estimated clinical risk score. An unreliability of a patient's clinical risk score is determined based at least in part on a feature of the patient and on a difference between the alternative probability estimate and the determined respective estimated clinical risk score.

Other embodiments of the present invention implement features of the above-described method in computer systems and computer program products.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
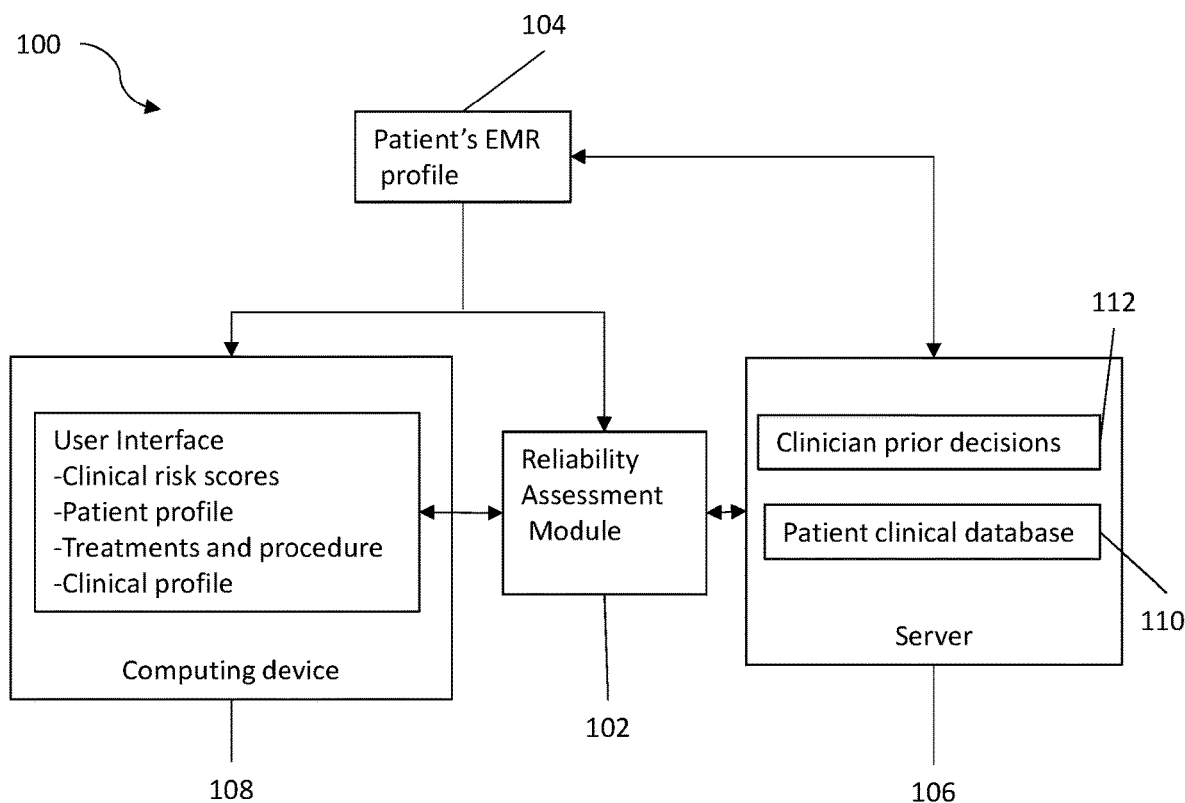
FIG. 1 depicts a block diagram of components of a system for assessing reliability of clinical risk prediction in accordance with one or more embodiments of the present invention.

The diagrams depicted herein are illustrative. There can be many variations to the diagrams or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

DETAILED DESCRIPTION

One or more embodiments of the present invention provide a clinical decision support system that provides a clinician with a patient-specific reliability measure for each clinical risk score provided by the system.

Conventional methods to estimate the reliability of the clinical risk scores generally fall into two categories: model-dependent and model-independent methods. Model-dependent methods generally report prediction confidence intervals that generally are calculated via least-squares estimation or by estimating the uncertainty in learned model parameters. Some neural network models evaluate whether there are sufficient data in the training set to make a prediction for a test sample or whether the test sample is similar to a region of the training set where the model has poor performance. However, this approach mandates the use of a particular type of classifier.

Model-independent approaches can be used with a variety of different predictive models, irrespective of the approach used to develop/train the model. Conventional model-independent approaches involve retraining the predictive model using an enhanced dataset that contains the original training set supplemented with new, unclassified data examples, where class labels for the unlabeled data are assigned based on the model's predictions. The model's performance before and after retraining are used to estimate the reliability of the predicted classes for the new data. However, a disadvantage of model-independent approaches is that, in practice, clinical datasets that are used to develop clinical risk scores are generally not available to users who would like to evaluate the reliability of a new prediction. Therefore, retraining a model with new data (or directly assessing how different a new patient is from the training examples) is generally not possible, given the rightful concerns over guarding patient privacy. These approaches can therefore only be implemented by those who have access to the original dataset used to train the risk model in question. More importantly, even if such data were available, retraining complex models can be computationally expensive, thereby making this approach infeasible for the average user who has access to limited computational resources, or who requires some estimate of the reliability of a given patient's prediction within a short time frame.

One model-independent approach, the "trust score", does not require that the classifier be retrained. However, to be computed it still requires access to the original training data, which may not be available to all health care providers. Furthermore, none of the above-described approaches have been evaluated in the setting of significant class imbalance. This is relevant as many clinical classification problems are associated with large class imbalance as the outcome of interest typically occurs in a small minority of patients.

Certain clinical scores may be evaluated for accuracy. For example, a clinical risk score may be applied to a million patients to determine if a clinical risk score is accurate. However, this is different than determining whether a clinical risk score is reliable for a particular patient. If the clinical risk score is accurate for ninety percent of the million patients, there is still one hundred thousand patients that the clinical risk score is inaccurate. Therefore, a need exists to proactively determine which patient belongs in the ninety percent and which patient belongs in the ten percent prior to the onset of treatment.

One or more embodiments of the present invention address one or more of the above-described shortcomings by providing a clinical decision support system that identifies patient subgroups that are associated with poor model performance, is model-independent, does not require retraining or access to the precise training dataset used to develop the original clinical risk model, and uses generative models to alleviate class imbalance.

Turning now to FIG. 1, a clinical decision support system is generally shown in accordance with one or more embodiments of the present invention. The system 100 includes a reliability assessment module 102, a server 106, and a database including a patient's electronic medical records (EMRs) profile 104. The reliability assessment module 102 includes a set of algorithms that can be stored on the computing device 108, the server 106, or some other computing device or memory.

The reliability assessment module 102 is operable to assess the reliability of a clinical risk score for an individual patient by computing an absolute value of a difference between an alternative estimated risk score and the original risk score. The reliability assessment module 102 then determines whether the difference is greater than a predefined threshold value. If the difference is greater than a threshold value, the original clinical risk score is deemed unreliable, if the difference is lower than the threshold, the original risk score is deemed reliable. The reliability assessment module 102 can further evaluate the difference in terms of multiple thresholds and further provide a degree of reliability or unreliability. For example, an original clinical risk score may have low unreliability or high unreliability based on respective thresholds.

The computing device 108, includes any computing device available to a clinician, such as a tablet, laptop, PC or the like. The computing device includes a user interface that provides the clinician with the clinical risk scores associated with a patient, a patient profile, any treatments or procedures that have been scheduled for the patient, a clinical, profile, and the reliability score for each respective clinical risk score.

In order to determine reliability, the following method can be followed:

Let $\vec{x}$ denote a random variable corresponding to a set of prognostic characteristics (the feature vector). Let $y \in \{0,1\}$ denote a random variable designating the true class label. For example, y=1 if a patient dies within a specified time after an initial diagnosis (the positive class) and y=0 if the patient does not die within the specified time (the negative class). Finally, let $f(\vec{x})$ be a clinical risk model that takes a feature vector as an input and outputs a risk score that can be used to estimate the probability of the true class label.

As clinical risk models generally report the probability of an adverse event, or some score that can be translated into a probability, $f(\vec{x})$ is considered to be a probability; (i.e., $f(\vec{x}) = P^E(y=1|\vec{x})$, where $P^E(y=1|\vec{x})$ is the probability that y=1 for a patient with feature vector $\vec{x}$. The superscript E designates that this probability is estimated from a training dataset). The metric to calculate the alternative risk score, $(y=1|\vec{x})$, uses the same data that was used to calculate $f(\vec{x})$ and is calculated using generative models for both the positive and negative classes (hence the superscript G). When $f(\vec{x})$ and $P^G(y=1|\vec{x})$ disagree, the training data is insufficient to provide a robust, trustworthy prediction.

The reliability assessment module 102 does not require training a new model using the training dataset, it can derive an expression for $(y=1|\vec{x})$ that is straightforward to compute. For example, using Bayes' theorem, express $P^G(y=1|\vec{x})$ as follows:

$$(y=1|\vec{x}) = \frac{(\vec{x}|y=1)P(y=1)}{P^G(\vec{x}|y=1)P(y=1) + P^G(\vec{x}|y=0)(1-P(y=1))},$$

where P(y=1) is the prevalence of the adverse outcome in the overall population and is estimated using the fraction of patients who belong to the positive class in the training dataset. Calculating $(y=1|\vec{x})$ requires an estimation of the likelihood of observing a given feature vector in the positive class, $P^G(\vec{x}|y=1)$, and the negative class, $P^G(\vec{x}|y=0)$. These likelihoods are estimated using trained generative models where one model generates feature vectors consistent with patients in the positive class, $(\vec{x}|y=1)$, and the other generates feature vectors consistent with patients in the negative class, $(\vec{x}|y=0)$. In practice, $P^G(\vec{x}|y=0)$ is agnostic to the type of generative model, for example, a multivariate normal (MVN) probability density function (pdf). More sophisticated models for the positive and negative class can be used when the training data are not well described by Gaussian probability density functions.

The above-described equation uses calculated definite integrals of multidimensional Gaussian pdfs, as the probabilities correspond to integrals over the pdfs. An alternative formula to describe a probability function can be described as follows:

$$U(\vec{x}) = \hat{y} \frac{\left(\frac{1-\hat{y}}{\hat{y}}\right) - \beta_{\vec{x}}^{-1}\left(\frac{1-P(y=1)}{P(y=1)}\right)}{1 + \beta_{\vec{x}}^{-1}\left(\frac{1-P(y=1)}{P(y=1)}\right)},$$

where $U(\vec{x})$ is the alternative clinical risk score. Furthermore, this formula uses the numerical calculation of a univariate probability density.

It should be appreciated that although two formulas have been described, the methods and system described herein can use a variety of formulas to discern an alternative risk score. The server 106 stores a database 110 with a collection of patient clinical data that includes information regarding demographics, allergies, diagnosis, laboratory results, operations, narratives, specialist's reports, vital signs, and any other appropriate patient-related data. The server 106 further stores a database of a clinician's prior decisions 112.

In embodiments where the reliability assessment module 102 is implemented as a neural network, neuromorphic systems include interconnected processor elements that act as simulated "neurons" and exchange "messages" between each other in the form of electronic signals. Similar to the so-called "plasticity" of synaptic neurotransmitter connections that carry messages between biological neurons, the connections in neuromorphic systems such as neural networks carry electronic messages between simulated neurons, which are provided with numeric weights that correspond to the strength or weakness of a given connection. The weights can be adjusted and tuned based on experience, making neuromorphic systems adaptive to inputs and capable of learning. For example, a neuromorphic/neural network for handwriting recognition is defined by a set of input neurons, which can be activated by the pixels of an input image. After being weighted and transformed by a function determined by the network's designer, the activations of these input neurons are then passed to other downstream neurons, which are often referred to as "hidden" neurons. This process is repeated until an output neuron is activated. Multiple pre-neurons and post-neurons can be connected through an array of resistive switching devices (RSDs), which naturally expresses a fully-connected neural network. In the descriptions here, any functionality ascribed to the system 100 that can be implemented using the processing system 500 applies.

Figure 2:
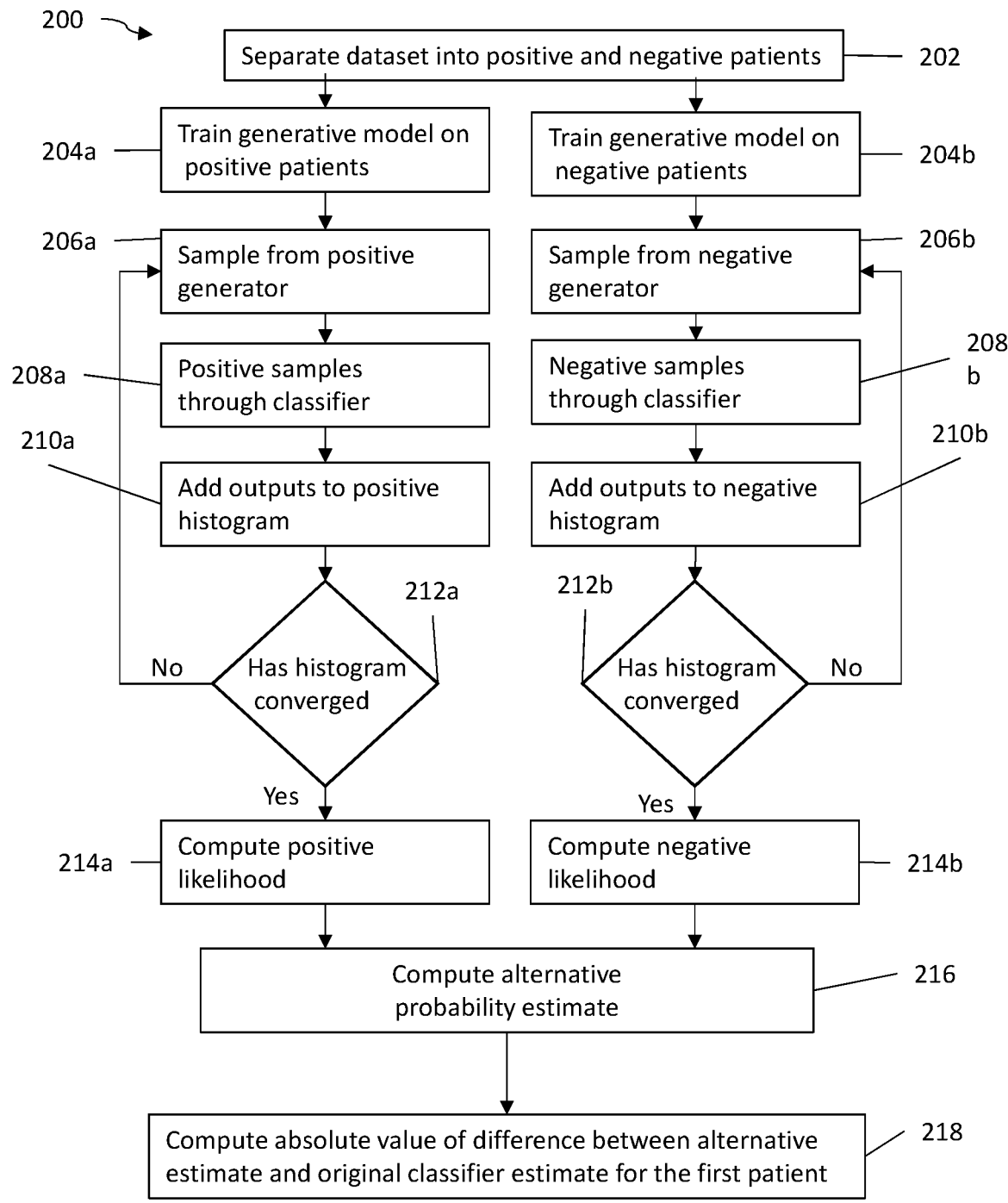
FIG. 2 depicts a flow diagram of a process for assessing reliability of clinical risk prediction in accordance with one or more embodiments of the present invention.
Figure 3:
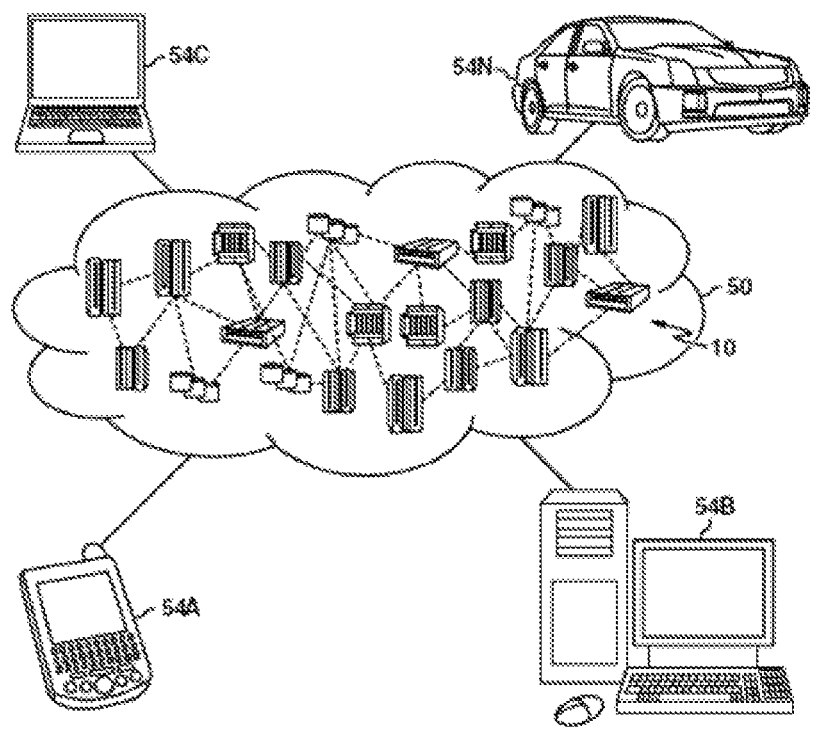
FIG. 3 depicts a cloud computing environment according to one or more embodiments of the present invention.

Referring to FIG. 2, a method for assessing the reliability of clinical risk prediction is shown. At block 202 a set of EMR data is retrieved from a database and segregated between positive and negative patient data sets. Positive patients are patients that have experienced some adverse outcome and negative patients are patients that have not experienced an adverse outcome. The EMRs are in either structured or unstructured format. Therefore, in some instances, the system may rely on metadata embedded in the EMRs or use natural language processing techniques to identify the patients as positive or negative. In many instances, the dataset will skew against positive patients resulting in a class imbalance.

At block 204a a generative model is trained using the positive patient data and at block 204b a generative model is trained using the negative patient data. This can be implemented by configuring and arranging the processing system 500 to execute machine learning (ML) algorithms. The generative model learns an underlying data distribution and is then able to generate synthetic data from the same distribution. For example, the system fits a distribution to a set of features identified for a particular patient population. Therefore, in the event that the positive patient data set is small, the system has an appropriate amount of data for subsequent steps.

At block 206a, the system samples synthetic data from the positive generator. At block 206b, the system samples synthetic data from the negative generator. At block 208a the system then processes samples from the original positive patient data set and the synthetic data set through a classifier, for example, the risk model, a plurality of risk models, including the original risk model whose reliability/unreliability is being verified. It should be appreciated that in the event that the system determines that the original data provides a large enough sample size, the system uses only the original data. At block 208b the system then processes samples from the original negative patient data set and the synthetic data set through a classifier, for example, a risk model, a plurality of risk models, including the original risk model whose reliability/unreliability is being verified. Each risk model provides an output for each patient, which can be mapped on to a positive patient and negative patient numerical distribution, for example, a histogram, a plot, a chart, or other distribution at block 210a and 210b.

At block 212a, the system determines whether the numerical distribution of the positive patients has converged. At block 212b, the system determines whether the numerical distribution of the negative patients has converged. If either numerical distribution has not converged, the system moves back to either block 206a or 206b and samples more data to process through the classifier. At block 214a, the system calculates a relative likelihood $P^G(\vec{x}|y=1)$ for use in the alternate risk estimate $(y=1|\vec{x})$. At block 214b, the system calculates a relative likelihood $P^G(\vec{x}|y=0)$ for use in the alternate risk estimate $(y=1|\vec{x})$. For example, by estimating a probability density function of the numerical distribution.

At block 216, the system calculates an alternative risk score for a patient currently receiving care, for example, by applying Bayes' theorem using the results from steps 214a and 214b.

At block 218, the system computes an absolute value of the difference between the alternative estimate and the original clinical risk score. The greater the difference between the estimates, the less reliable the original clinical risk score is.

The reliability determinations for multiple clinical risk scores are calculated based on the samples generated. For example, reliability determinations for clinical risk scores for patients that have diabetes and prior heart issues are calculated. Reliability determinations for clinical risk scores for patients with diabetes that had no prior heart issues are also calculated. As a clinician meets with a patient, each of the patient features is inputted into the clinician's computer system. Then as the clinical risk scores for the patient are provided, the system matches the patient's individual features with a reliability/unreliability determination derived from data from patients having similar features. The system displays whether the clinical risk score is reliable/unreliable for that particular patient. Based on an indication of reliability, the system reviews the past decisions of the clinician(s) and retrieves a list of suggested treatments or medications based on the past decisions. In some embodiments of the present invention, the system further removes clinical risk scores that are determined to be unreliable for that patient from the clinician's user interface, this can occur during a patient's visit or automatically before a subsequent visit, but after the initial visit.

Based on an indication of reliability or unreliability, the system is operable to modify a clinician's user interface. For example, in a typical setting a user interface may include frame or a drop-down menu that includes descriptive titles with links for each clinical risk score of a patient. For example, the list includes descriptive titles such as "ADA Diabetes Risk", "Breast Cancer Risk", and "CAGE alcohol screening". A clinician can, through text, voice command, cursor, touch or other appropriate method, select one of these descriptive titles/links and receive an associated clinical risk score. Based on the unreliability scores, the system is operable to modify the visual appearance of the descriptive titles to alert the clinical, prior to viewing the actual clinical risk score. For example, a color of the descriptive titles can be modified to signal a degree of unreliability or reliability. High unreliability clinical risk scores can have descriptive titles listed in red, medium unreliability scores can have descriptive titles in orange, and low unreliability clinical risk scores can have descriptive titles in green. In this sense, the clinician is alerted in regard to an unreliability prior to viewing the score.

In other embodiments, the descriptive titles can be rearranged in order of reliability or unreliability. In yet even other embodiments, the descriptive titles/links can be subdivided from a single frame to multiple frames, in which each frame includes descriptive titles based on a relative unreliability. For example a first frame may include descriptive titles/links for clinical risk scores that have high unreliability and a second frame may include descriptive titles/links for clinical risk scores that have low unreliability.

In yet another embodiment, the system reviews the patient's EMR to determine the primary care physician, pharmacist, or other health care professionals currently providing health care or have previously provided. In some iterations, the system further determines the nature of the treatment. Upon learning the identity, the system issues an electronic communication to the primary care physician, pharmacist, or other health care professionals that a clinical risk score has been deemed unreliable. In some iterations, the communications are based on whether the treatment or medication provided relates to the clinical risk score. In this sense, health care professionals without access to the unreliability score have access to the determination. Therefore, other health care professionals can alter their treatment based on the understanding of the unreliability of the clinical risk scores.

Based on an indication of an unreliable clinical risk score, the physician would integrate the unreliability score into their clinical decision making process. For example, a number of clinical guidelines suggest that patients who are at high risk of death, as assessed via standard clinical risk scores, after a myocardial infarction, should undergo coronary angiography—an invasive procedure associated with its own risks. However, if the associate clinical risk score is deemed unreliable for that patient, then the clinician may decide to forgo coronary angiography for that patient. In general, the physician may follow or hold-off applying more aggressive counseling, applying a certain screening (e.g., adding a patch monitor for atrial fibrillation patients), favoring adding a certain medication (or changing a dose), performing or holding-off a biopsy, etc. depending on how unreliable the associated risk score is. In another embodiment, several commonly used scores may be calculated for the patient (e.g., MELD, Framingham risk score, EHR-AF, CHARGE), and each score would also be associated with an unreliability rank. The physician may decide to avoid using the one or more scores that were found unreliable and prefer the one or more scores that were associated with low unreliability ranks. A physician may decide also to avoid the use of any scores, and follow his/her experience or judgment for further treatments or holding-off treatments.

The above-described method has been tested using real-world data. The unreliability metric, $U(\vec{x})$, is a function of the risk model, $f(\vec{x})$, the prevalence of the outcome of interest in the overall population, $P(y=1)$, and the relative likelihood ratio of the positive and negative classes arising from the generative models, $\beta_{\vec{x}}$. To understand how each of these quantities affects the unreliability estimate, $U(\vec{x})$ was computed for a range of input parameters and then the average value of $U(\vec{x})$ was calculated as a function of the risk model prediction. Two limiting cases were considered: i) when there is no class imbalance in the training data ($P(y=1)=0.5$), and ii) when the positive class ($y=1$) is in the minority ($P(y=1)=0.01$). When there is no class imbalance on average, values of the clinical risk score that are close to 0 or 1 are slightly more unreliable than values close to 0.5, which is equal to the prevalence of the outcome in the population. By contrast, on average, when there is a significant class imbalance, unreliable predictions are more likely to occur in patients who are predicted to be at high risk. In other words, when there is a relatively small number of patients who belong to the positive class, and consequently few positive examples for the clinical model to learn from, positive predictions are, on average, more likely to have high values of $U(\vec{x})$.

$U(\vec{x})$ was computed for the Global Registry of Acute Coronary Events (GRACE) risk score, which quantifies the risk of death 6-months after presenting with an acute coronary syndrome. The goal was to compute $U(\vec{x})$ for patients in the GRACE registry, identify the most unreliable predictions in this cohort, and evaluate the performance of the GRACE score on this "unreliable" subgroup.

$U(\vec{x})$ was computed for all patients in the GRACE test set and the accuracy of predictions that have high unreliability relative to those who have a lower unreliability score was evaluated. First, it should be noted, patients who are predicted to be high risk are more likely, on average, to have high unreliability scores. Calibration curves demonstrated that patients within the upper 50% of unreliability values tended to overestimate a patient's risk of death, while predictions within the lower 50% of unreliability values were well-calibrated.

To more quantitatively assess the accuracy of predictions arising from the GRACE score in unreliable patient subgroups the Brier score was relied upon. Formally, the Brier score is the mean square error between the prediction and the true class label (i.e., lower Brier scores indicate more accurate predictions). However, the Brier score itself is dependent on the prevalence of the outcome of interest, and consequently can be difficult to interpret when assessing the performance of a classifier on subgroups that have different expected outcome rates (i.e., the Brier score tends to be lower when the incidence of the outcome is low). Therefore, the Brier score was normalized by a Brier null model, which corresponds to the scenario where every patient is predicted to have a risk equal to the prevalence of the outcome in that respective subgroup. Predictions corresponding to the top 50% of $U(\vec{x})$ values have a modest, yet statistically significant, reduced accuracy, as measured via a normalized Brier score, relative to predictions that fall within the lower 50% of $U(\vec{x})$ values.

The AUC (or C-statistic) for patients was computed to assess the discriminatory ability of the GRACE risk score in patients who have unreliable predictions. The GRACE score similarly has relatively poor discriminatory ability in predictions that fall within the top 50% of $U(\vec{x})$ values.

Calibration curves for predictions that fall within the top 1% of $U(\vec{x})$ values (henceforth referred to as the "most unreliable predictions") similarly underestimate the actual risk of death. Similarly, the prediction error, measured via a normalized Brier score, for the subgroup consisting of the most unreliable predictions was significantly higher than the error associated with all other patients in the dataset. The AUC for the most unreliable subgroup was also significantly reduced relative to the AUC of the remainder of the test data set, suggesting that predictions for the most unreliable subgroup have significantly reduced discriminatory ability relative to the remainder of the dataset.

To assess whether these findings were unique to the unreliability metric, or whether they generalized to other metrics that strive to quantify the reliability in a given risk prediction, an alternate metric was computed that purports to quantify when a given classifier's result should be trusted. The trust score measures the agreement between the classifier and a nearest-neighbor classifier on a testing example. At a high level, the score measures the distance between a given test set example and training examples in each class (i.e., the set consisting of training examples that have the outcome of interest and the set of training examples that do not). For a binary classification problem, the trust score is the ratio between the distance to the alternate class and the distance between the predicted class. Unlike the herein-described unreliability metric, which associates high values of $U(\vec{x})$ with unreliable predictions, low trust scores denote predictions that are untrustworthy as they are more similar to training examples in the class that is different from the one that the model predicts.

Calibration curves for the most untrustworthy predictions (i.e., predictions within the lowest 1% of trust values) demonstrated that the method identifies poorly calibrated risk estimates. Predictions within the top 1% of trust score values underestimated the actual patient risk. However, predictions in the remainder of the dataset tended to overestimate patient risk. Moreover, normalized Brier scores suggested that the most untrustworthy predictions have errors that are similar to that of predictions in the remainder of the dataset. Calculated AUCs of both subgroups suggest that the discriminatory ability of the classifier is similar in both the most untrustworthy subgroup and in the subgroup containing all other remaining patients.

To determine whether the findings generalized to other outcomes and risk scores, a model was generated to predict the risk of in-hospital stroke in patients presenting with an acute coronary syndrome. Unreliability scores were again computed for all patients. The most unreliable patients form a subgroup whose risk is underestimated by the model, while the model was well calibrated for all other patients in the dataset. The average error for patients in the most unreliable subgroup was larger than the average error for other patients in the dataset, as expected, although this difference is not statistically significant. The discriminatory ability of the classifier was reduced in the most unreliable cohort, relative to the classifier's discriminatory ability in the remainder of the data.

Trust score values were again computed for the Stroke Risk model predictions and the performance of the subgroup consisting of the most untrustworthy predictions was evaluated. Similar to what was observed with the trust calculations on the GRACE risk model, predictions with the highest trust score underestimate the overall risk of stroke. However, the average prediction error associated with this untrustworthy subgroup is lower than that of the other patients in the dataset, and the corresponding difference is statistically significant. Moreover, the discriminatory ability of the stroke risk score was actually higher in the untrustworthy subgroup.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls)

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is a service oriented with a focus on statelessness, low coupling, modularity, and semantic interoperability. At the heart of cloud computing is an infrastructure that includes a network of interconnected nodes.

Figure 4:
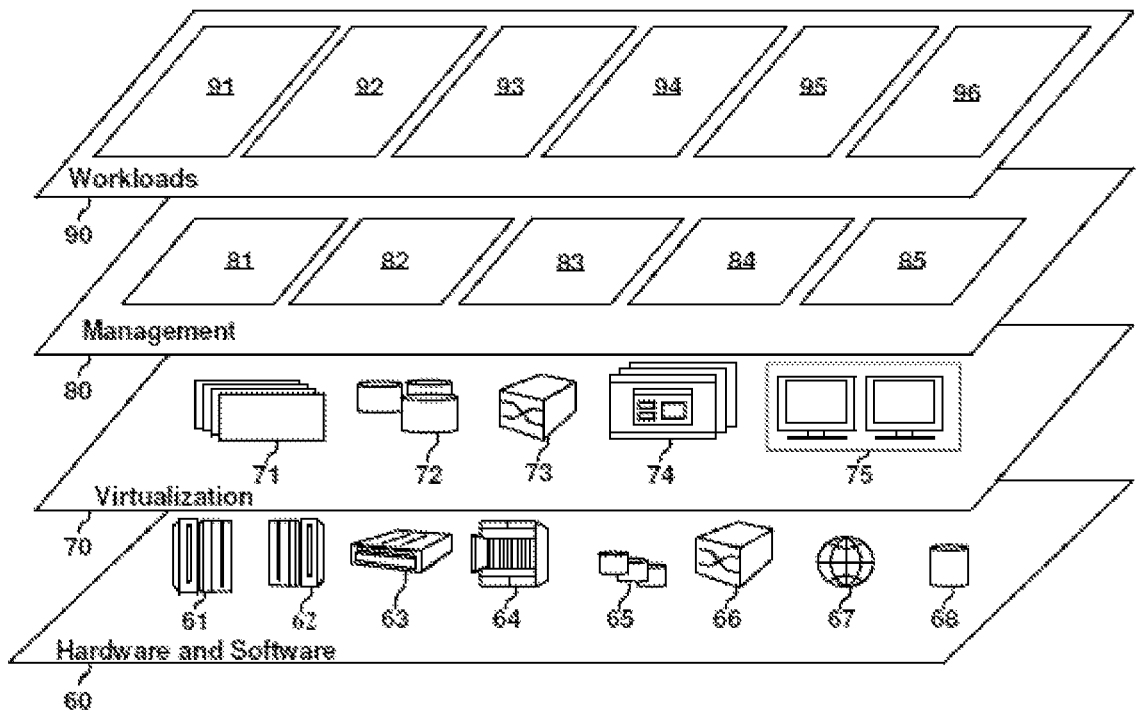
FIG. 4 depicts abstraction model layers according to one or more embodiments of the present invention.

Referring now to FIG. 4, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
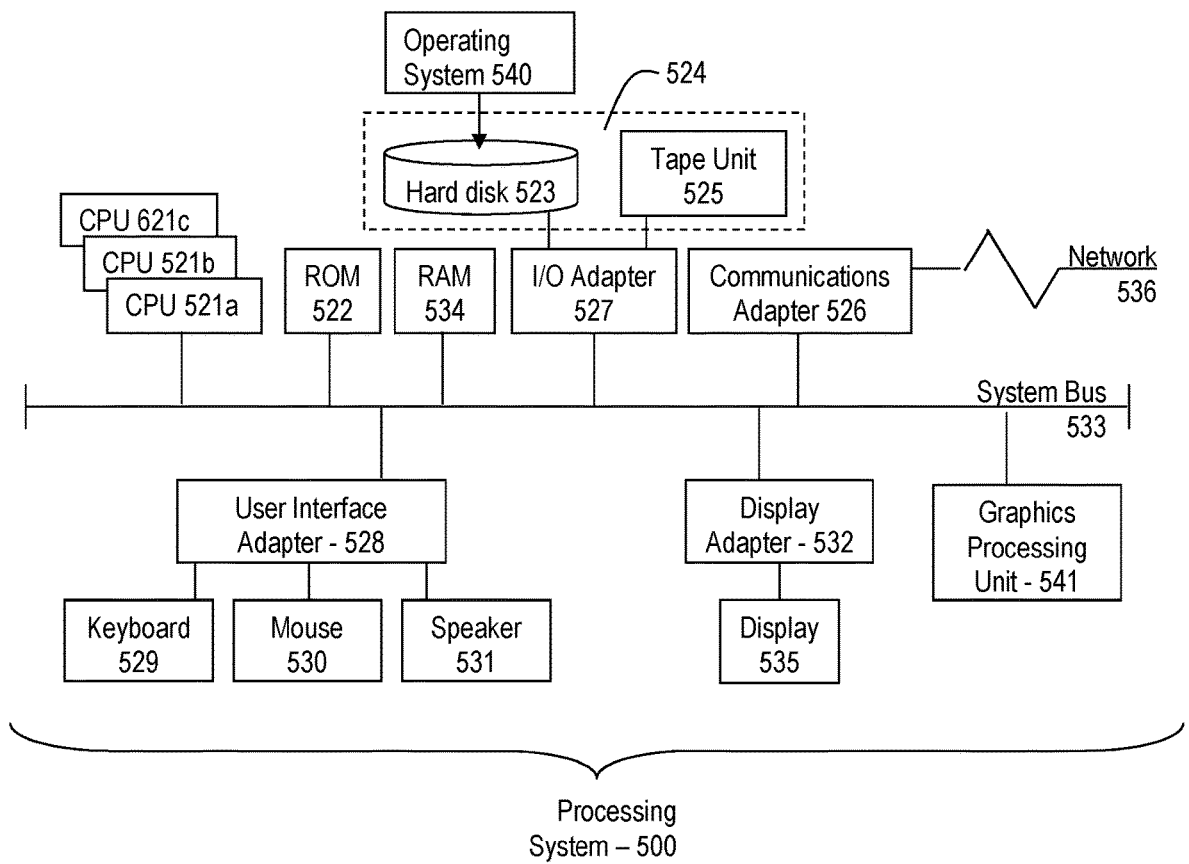
FIG. 5 depicts a block diagram of a computer system for use in implementing one or more embodiments of the present invention.

Referring now to FIG. 5, a set of functional abstraction layers provided by cloud computing environment 50 (FIG. 1) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and clinical risk score evaluation 96.

It is understood that the present disclosure is capable of being implemented in conjunction with any other type of computing environment now known or later developed. For example, FIG. 5 depicts a block diagram of a processing system 500 for implementing the techniques described herein. In examples, the processing system 500 has one or more central processing units (processors) 521a, 521b, 521c, etc. (collectively or generically referred to as processor(s) 521 and/or as processing device(s)). In aspects of the present disclosure, each processor 521 can include a reduced instruction set computer (RISC) microprocessor. Processors 521 are coupled to system memory (e.g., random access memory (RAM) 524) and various other components via a system bus 533. Read only memory (ROM) 522 is coupled to system bus 533 and may include a basic input/output system (BIOS), which controls certain basic functions of the processing system 500.

Further depicted are an input/output (I/O) adapter 527 and a network adapter 526 coupled to the system bus 533. I/O adapter 527 may be a small computer system interface (SCSI) adapter that communicates with a hard disk 523 and/or a storage device 525 or any other similar component. I/O adapter 527, hard disk 523, and storage device 525 are collectively referred to herein as mass storage 534. Operating system 540 for execution on processing system 500 may be stored in mass storage 534. The network adapter 526 interconnects system bus 533 with an outside network 536 enabling processing system 500 to communicate with other such systems.

A display (e.g., a display monitor) 535 is connected to the system bus 533 by display adapter 532, which may include a graphics adapter to improve the performance of graphics intensive applications and a video controller. In one aspect of the present disclosure, adapters 526, 527, and/or 532 may be connected to one or more I/O busses that are connected to the system bus 533 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 533 via user interface adapter 528 and display adapter 532. An input device 529 (e.g., a keyboard, a microphone, a touchscreen, etc.), an input pointer 530 (e.g., a mouse, trackpad, touchscreen, etc.), and/or a speaker 531 may be interconnected to system bus 533 via user interface adapter 528, which may include, for example, a Super I/O chip integrating multiple device adapters into a single integrated circuit In some aspects of the present disclosure, the processing system 500 includes a graphics processing unit 537. Graphics processing unit 537 is a specialized electronic circuit designed to manipulate and alter memory to accelerate the creation of images in a frame buffer intended for output to a display. In general, graphics processing unit 537 is very efficient at manipulating computer graphics and image processing and has a highly parallel structure that makes it more effective than general-purpose CPUs for algorithms where processing of large blocks of data is done in parallel.

Thus, as configured herein, the processing system 500 includes processing capability in the form of processors 521, storage capability including system memory (e.g., RAM 524), and mass storage 534, input means such as keyboard 529 and mouse 530, and output capability including speaker 531 and display 535. In some aspects of the present disclosure, a portion of system memory (e.g., RAM 524) and mass storage 534 collectively store the operating system 540 to coordinate the functions of the various components shown in the processing system 500.

The term "about" is intended to include the degree of error associated with measurement of the particular quantity based upon the equipment available at the time of filing the application.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

Computer Program Product Boilerplate Follows

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

End of Computer Program Product Boilerplate

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
using a neural network as a trained risk model for identifying a respective estimated clinical risk score for each of a first group of patients having an adverse outcome within a specified time to a treatment and a second group of the patients having not experienced the adverse outcome within the specified time to the treatment, the respective estimated clinical risk score for the first group of the patients and the second group of the patients having been determined by the trained risk model using a set of inputs as original data, there being an imbalance in a number of the patients in the first group and the second group;
training a generative model using the first group of the patients having the adverse outcome as training data within the specified time to the treatment, wherein the generative model learns an underlying data distribution in order to generate synthetic first group data, wherein the generative model is a multivariate normal probability density function, wherein the training data of the generative model comprises a portion used to train the neural network;

generating synthetic first group data using the generative model to alleviate the imbalance, the synthetic first group data generated by the generative model is based at least in part on the first group of the patients having the adverse outcome within the specified time to the treatment, the generative model having been trained using the first group of the patients, the generative model comprising machine learning algorithms, wherein the synthetic first group data augments the number of the patients in the first group;

generating an alternative probability estimate using the set of inputs used to determine each respective estimated clinical risk score, wherein the alternative probability estimate is based at least in part on the original data from electronic medical records of the patients of the first group and the second group in combination with the synthetic first group data generated by the generative model;

determining an unreliability of a patient's clinical risk score based at least in part on a feature of the patient and on a difference between the alternative probability estimate and the determined respective estimated clinical risk score; and responsive to a determination of unreliability associated with the patient, alerting a clinician via a user interface of the unreliability associated with the patient in order to result in a modification in medication for the patient, the alerting causing an avoidance of an invasive procedure and its associated risk for the patient.

2. The computer-implemented method of claim 1, further comprising:

generating synthetic second group data using a generative model, wherein the alternative probability estimate is based at least in part on original data from electronic medical records of the patients of the first group and the second group and the synthetic data.

3. A computer-implemented method of claim 1, wherein a class imbalance skews in favor of the second group.

4. The computer-implemented method of claim 1, wherein each patient from the first group shares a feature, and wherein each patient from the second group shares a feature.

5. The computer-implemented method of claim 1, further comprising:

displaying the unreliability of the clinical risk score on a user interface, wherein the user interface is modified from an original format to provide a visual alert of an unreliability of the clinical risk score.

6. A system comprising:

a memory having computer readable instructions; and one or more processors for executing the computer readable instructions, the computer readable instructions controlling the one or more processors to perform operations comprising:

using a neural network as a trained risk model for identifying a respective estimated clinical risk score for each of a first group of patients having an adverse outcome within a specified time to a treatment and a second group of the patients having not experienced the adverse outcome within the specified time to the treatment, the respective estimated clinical risk score for the first group of the patients and the second group of the patients having been determined by the trained risk model using a set of inputs as original data, there being an imbalance in a number of the patients in the first group and the second group;

training a generative model using the first group of the patients having the adverse outcome as training data within the specified time to the treatment, wherein the generative model learns an underlying data distribution in order to generate synthetic first group data, wherein the generative model is a multivariate normal probability density function, wherein the training data of the generative model comprises a portion used to train the neural network;

generating the synthetic first group data using the generative model to alleviate the imbalance, the synthetic first group data generated by the generative model is based at least in part on the first group of the patients having the adverse outcome within the specified time to the treatment, the generative model having been trained using the first group of the patients, the generative model comprising machine learning algorithms, wherein the synthetic first group data augments the number of the patients in the first group;

generating an alternative probability estimate using the set of inputs used to determine each respective estimated clinical risk score, wherein the alternative probability estimate is based at least in part on the original data from electronic medical records of the patients of the first group and the second group in combination with the synthetic first group data generated by the generative model;

determining an unreliability of a patient's clinical risk score based on a difference between the alternative probability estimate and the determined respective estimated clinical risk score; and responsive to a determination of unreliability associated with the patient, alerting a clinician via a user interface of the unreliability associated with the patient in order to result in a modification in medication for the patient, the alerting causing an avoidance of an invasive procedure and its associated risk for the patient.

7. The system of claim 6, the operations further comprising:

generating synthetic second group data a generative model, wherein the alternative probability estimate is based at least in part on original data from electronic medical records of the patients of the first group and the second group and the synthetic data.

8. The system of claim 6, wherein a class imbalance skews in favor of the second group.

9. The system of claim 6, wherein the first group comprises patients that have a positive outcome within a specified time to a treatment, the positive outcome being associated with the adverse outcome, and wherein the second group comprises patients that have a negative outcome with the specified time to the treatment.

10. The system of claim 6, wherein each patient from the first group shares a feature, and wherein each patient from the second group shares a feature.

11. The system of claim 6, the operations further comprising:

displaying the reliability of the clinical risk score on a user interface, wherein the user interface is modified from an original format to provide a visual alert of an unreliability of the clinical risk score.

12. A computer program product comprising a computer readable storage medium having program instructions embodied therewith, the program instructions executable by a processor to cause the processor to perform operations comprising:
identifying a respective estimated clinical risk score for each of a first group of patients comprising certain ones of the patients having an adverse outcome within a specified time to a treatment and a second group of the patients comprising other ones of the patients having not experienced the adverse outcome within the specified time to the treatment, the respective estimated clinical risk score for the first group of the patients and the second group of the patients having been determined by a trained risk model using a set of inputs as original data, there being an imbalance in a number of the patients in the first group and the second group;
training a generative model using the first group of the patients having the adverse outcome as training data within the specified time to the treatment, wherein the generative model learns an underlying data distribution in order to generate synthetic first group data, wherein the generative model is a multivariate normal probability density function, wherein the training data of the generative model comprises a portion used to train the neural network;
generating the synthetic first group data using the generative model to alleviate the imbalance, the synthetic first group data generated by the generative model is based at least in part on the first group of the patients having the adverse outcome within the specified time to the treatment, the generative model having been trained using the first group of the patients, wherein the synthetic first group data augments the number of the patients in the first group;
generating an alternative probability estimate using a same set of inputs used to determine each respective estimated clinical risk score, wherein the alternative probability estimate is based at least in part on the original data from electronic medical records of the patients of the first group and the second group in combination with the synthetic first group data generated by the generative model;
determining an unreliability of a patient's clinical risk score based on a difference between the alternative probability estimate and the determined respective estimated clinical risk score; and
responsive to a determination of unreliability associated with the patient, alerting a clinician via a user interface of the unreliability associated with the patient in order to result in a modification in medication for the patient, the alerting causing an avoidance of an invasive procedure and its associated risk for the patient.

13. The computer program product of claim 12, the operations further comprising:
generating synthetic second group data a generative model, wherein the alternative probability estimate is based at least in part on original data from electronic medical records of the patients of the first group and the second group and the synthetic data.

14. The computer program product of claim 12, wherein a class imbalance skews in favor of the second group.

15. The computer program product of claim 12, wherein the first group comprises patients that have a positive outcome within a specified time to a treatment, the positive outcome being associated with the adverse outcome, and wherein the second group comprises patients that have a negative outcome with the specified time to the treatment.

16. The computer program product of claim 12, wherein each patient from the first group shares a feature, and wherein each patient from the second group shares a feature.

17. The computer-implemented method of claim 1, further comprising responsive to the determination of the unreliability associated with the patient, causing an electronic communication to be sent to at least one professional selected from the group consisting of a primary care physician or a pharmacist.

* * * * *